United States Patent
Wolf et al.

(10) Patent No.: US 7,144,412 B2
(45) Date of Patent: Dec. 5, 2006

(54) GOLD SUTURE AND METHOD OF USE IN WOUND CLOSURE

(75) Inventors: Bradley R. Wolf, Cincinnnati, OH (US); Igor A. Bogin, Alma-Aty (KZ); Ruben A. Bogin, Westerville, OH (US)

(73) Assignee: Wolf Medical Enterprises, Inc., Cincinnati, OH (US)

( * ) Notice: Subject to any disclaimer, the term of this patent is extended or adjusted under 35 U.S.C. 154(b) by 332 days.

(21) Appl. No.: 10/606,191

(22) Filed: Jun. 25, 2003

(65) Prior Publication Data

US 2004/0267314 A1    Dec. 30, 2004

(51) Int. Cl.
*A61B 17/04*    (2006.01)

(52) U.S. Cl. .................. 606/228; 606/230; 128/216

(58) Field of Classification Search ......... 606/228–230
See application file for complete search history.

(56) References Cited

U.S. PATENT DOCUMENTS

| | | | |
|---|---|---|---|
| 4,517,997 A | 5/1985 | Forchetti | |
| 4,602,636 A | 7/1986 | Noiles | |
| 4,946,467 A * | 8/1990 | Ohi et al. ................ | 606/228 |
| 5,089,012 A | 2/1992 | Prou | |
| 5,330,530 A | 7/1994 | Hastings | |
| 5,333,625 A | 8/1994 | Klein | |
| 5,454,834 A * | 10/1995 | Boebel et al. ............. | 606/228 |
| 5,639,278 A * | 6/1997 | Dereume et al. .......... | 623/1.13 |
| 5,645,558 A | 7/1997 | Horton | |
| 5,814,068 A | 9/1998 | Koike et al. | |
| 5,931,855 A * | 8/1999 | Buncke ..................... | 606/228 |
| 6,030,377 A * | 2/2000 | Linhares et al. ............. | 606/7 |
| 6,086,578 A | 7/2000 | Adamyan et al. | |
| 6,113,621 A | 9/2000 | Wiktor | |
| 6,197,043 B1 * | 3/2001 | Davidson ................... | 606/228 |
| 6,224,675 B1 * | 5/2001 | Prentice et al. ............ | 118/669 |
| 6,264,675 B1 | 7/2001 | Brotz | |
| 6,478,809 B1 | 11/2002 | Brotz | |
| 6,686,437 B1 * | 2/2004 | Buchman et al. ........... | 528/170 |

FOREIGN PATENT DOCUMENTS

FR    2747908    * 10/1997

* cited by examiner

*Primary Examiner*—Gary Jackson
(74) *Attorney, Agent, or Firm*—Thompson Hine LLP

(57) ABSTRACT

A method of wound closure comprising providing a gold suture and closing the laceration with the gold suture. The laceration is closed by: inserting the suture into the dermis and through the subcutaneous fat layer on one side of the laceration; inserting the suture at the base of the laceration; inserting the suture through the subcutaneous fat layer and into the dermis on the other side of the laceration to form a loop under the skin; repeating the steps in another insertion 3 to 5 mm from the loop in a continuous or interrupted manner to close the laceration; and tightening the suture line by applying tension to the loops to bring one side of the laceration into contact with the other side of the laceration.

19 Claims, 3 Drawing Sheets

GOLD SUTURE AND METHOD OF USE IN WOUND CLOSURE

BACKGROUND

The invention concerns surgical procedures, and in particular relates to surgical methods using a gold suture. The methods include closing wounds, tissue support and repair of internal tissues such as tendons and ligaments.

Sutures have been used in surgical procedures to close surgical and traumatic wounds, to close the skin in plastic surgery, to secure damaged or severed tendons, muscles or other internal tissues, and in microsurgery on nerves and blood vessels, all for holding tissues together to support healing and regrowth. Such sutures are attached to the shank end or trailing end of a needle. The sutures can be a monofilament or a braided material and many are available as a one-piece unit pre-attached to a needle. Sutures can be of non-absorbable material such as silk, nylon, polyester, polypropylene or cotton, or of bioabsorbable material such as polymers and copolymers of glycolic and lactic acid. Nevertheless, the problem with non-absorbable sutures is that they can still have some slow degradation which causes a decrease in tensile strength. Additionally, they frequently become the source of tissue reaction and infection/inflammation. This could result in excessive scar formation or wound or tissue dehiscence. The use of bioabsorbable sutures are also limited and not an option in wounds requiring high tension because after degradation they leave the skin scar without support for underlining tissue which may cause the scar to increase in size. Examples of surgical procedures requiring high tension include the scalp reduction procedures or hair restoration procedures.

Loop stitching has been the primary procedure, particularly to close a surface wound, whether an accidental or surgical wound. Such looped sutures, which are similar to the simplest method of seaming two pieces of fabric together, can leave scars on the fully healed wound. Although this can be alleviated in some cases and to some extent by using very fine suture material (e.g. 100 microns in diameter), the loop stitching still can cause very visible scars, and for adequate closure of some wounds the suture material must be of a high tensile strength and thus a larger diameter, increasing scarring.

Surface adhesive tapes are often used on the skin to hold small wounds closed to permit healing, but-these have relatively low tensile strength and are not useful in many situations. Another approach, sometimes practical, has been the use of staples for holding closed a wound for healing. The staples have relatively high strength and save time, but are not as accurate as sutures, and are bulky and painful to remove.

Surgical sutures having barbs, for providing a non-slip attribute in one direction, are shown in U.S. Pat. No. 3,123,077. In addition, in about the 1960s a metal tendon suture was produced and tried, the suture having a single, large barb for gripping of the tendon tissue. The metal suture was not successful and may no longer be available, and the technique is outdated. U.S. Pat. Nos. 5,425,747 and 5,584,859 disclose a type of suture having external barbs for holding together the two sides of an open wound. The disclosed devices had lateral members with barbs, the lateral members being shaped somewhat like small spears which were to be inserted into the tissue on opposite sides of a wound, to bind the wound together. The arrays of barbed, parallel-extending spears on both sides of the wound were held together by a central body member which lay within the wound and parallel to the length of the wound and which was secured to the barbed spears on each of the two sides. All of these components were described as being of bioabsorbable material. In the '859 patent, stretchable elastic connectors secured the spear-like lateral members to the central body member, so as to impose a tension force to pull the two sides of the wound together.

The spear-like barbed lateral members of the two described patents were required to be pushed into the patient's tissue, and therefore had to be of sufficient stiffness and large enough diameter such as to be capable of being pushed into the tissue. The resulting tissue securement would appear to be bulky and painful. The larger foreign body would tend to cause excessive scarring and would tend to increase the possibility for wound infections.

It is an object of the invention to improve on suturing techniques for closing wounds and severed tissues, and for performing cosmetic surgery such as face lifts and hair transplants, while minimizing scarring and providing a strong retaining force between the two side of tissue.

SUMMARY OF THE INVENTION

A method of wound closure comprising providing a gold suture and closing the laceration with the gold suture. The laceration is closed by: inserting the suture into the dermis and through the subcutaneous fat layer on one side of the laceration; inserting the suture at the base of the laceration; inserting the suture through the subcutaneous fat layer and into the dermis on the other side of the laceration to form a loop under the skin; repeating the steps in another insertion 3 to 5 mm from the loop in a continuous or interrupted manner to close the laceration; and tightening the suture line by applying tension to the loops to bring one side of the laceration into contact with the other side of the laceration. In an embodiment of the invention, knots are formed on both ends of the suture, leaving the entire suture under the skin. In another embodiment of the invention, the suture is inserted between hair follicles in hair-bearing skin regions. In yet another embodiment of the invention, single or multiple interrupted sutures is inserted in the same intradermal pattern. In a preferred embodiment of the invention, the suture is a braided suture comprising gold and bioabsorbable threads.

This method provides an efficient procedure for closing wounds, incisions and severed tissues such as tendons, joint capsules, aponeurosis and ligaments. Furthermore, the method may also be used to perform cosmetic surgeries such as hair restoration.

DETAILED DESCRIPTION

The invention is directed to the use of gold sutures in wound closure. A method is directed to closing tissue under tension using a gold suture. The suture is located under the epidermis to minimize scarring and provide a strong permanent retaining force between the two sides of tissue.

Gold threads are useful as sutures because gold is an inert material compatible with the body and almost never cause infection or inflammation when implanted in body tissue and left in place. Typically, the gold sutures are 22 carats and above. Non-absorbable threads such as nylon sutures are used in certain surgical operations but need to be removed eventually. Furthermore, one problem with non-absorbable sutures is that they can still have some slow degradation which causes a decrease in tensile strength. Additionally, they frequently become the source of tissue reaction and infection/inflammation. This could result in excessive scar formation or wound or tissue dehiscence. The advantage of gold sutures is that they can remain in the body and do not need to be removed.

Figure 1:
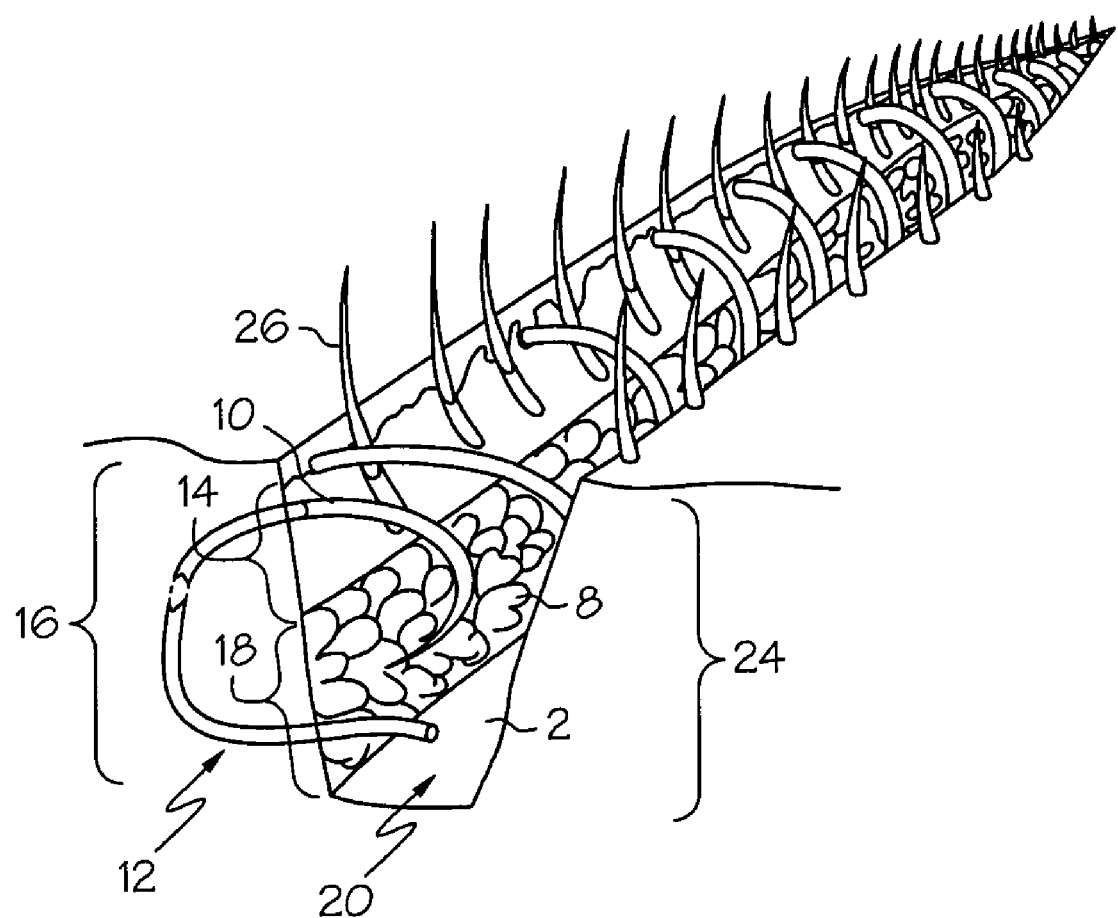
FIG. 1 is a view an embodiment of the wound closure method of the invention.
Figure 2:
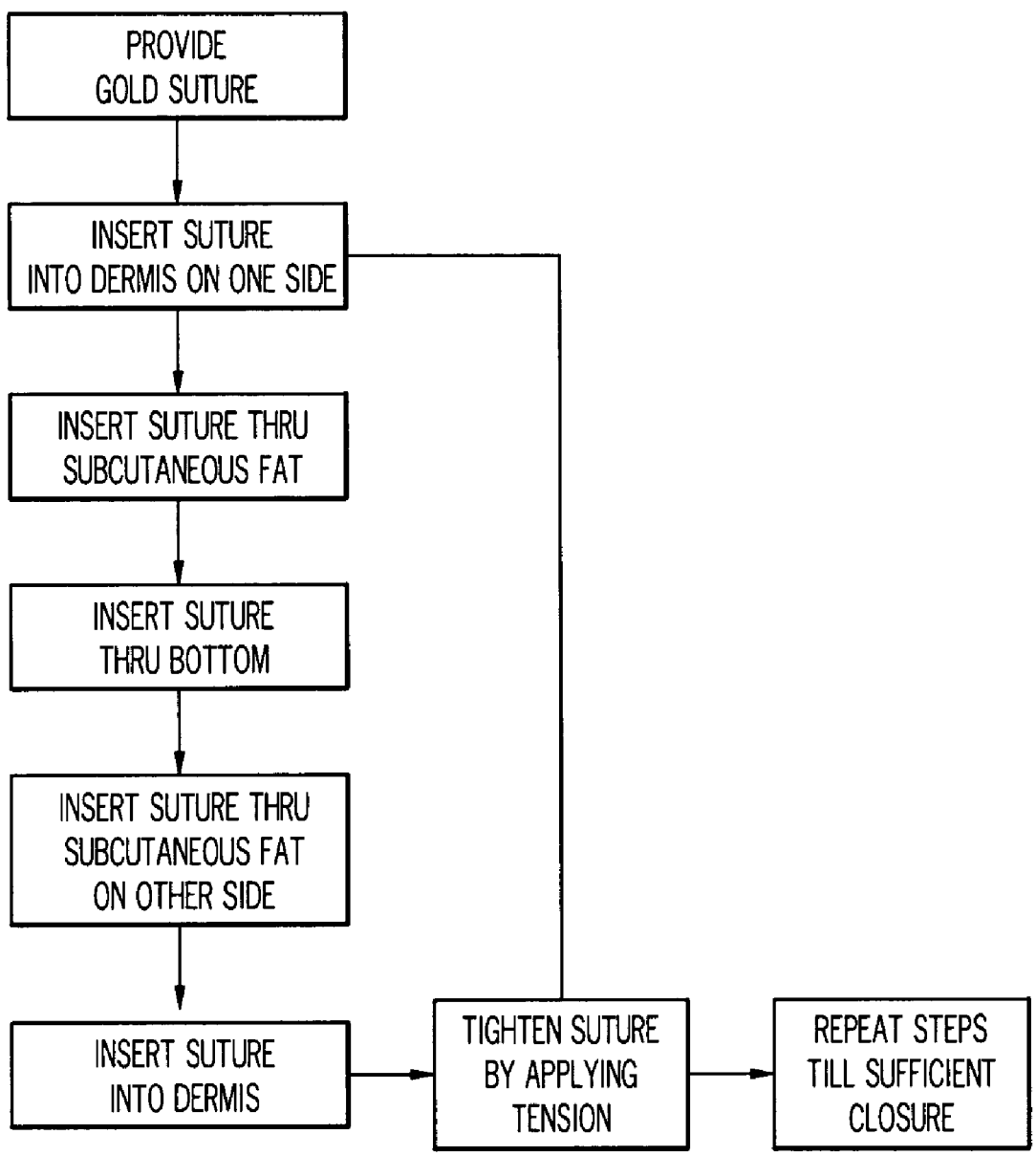
FIG. 2 is a diagram of the method of the invention.

Accordingly, a method using gold sutures to close wounds is described wherein the sutures are left in place permanently. In an embodiment of the invention shown in FIG. 1, the method for wound closure with a gold suture begins by inserting a surgical needle 10 with the attached gold suture 12 into the dermis 14 at one side 16 of the laceration, penetrating through the subcutaneous fat 18. The needle 10 is positioned vertically in the dermis 14 and inserted through the base 20 of the wound through part of the aponeurosis and then inserted through the subcutaneous fat 18 into the dermis 14 on the other side 24 of the laceration to form a loop under the skin. A continuous insertion is made approximately 3 to 5 mm from the previous loop and the intradermal suture loop technique is repeated. The suture line is then tightened by applying tension to one loop after another to bring the two sides of the laceration together; knots are formed on both ends of the suture and left under the skin. Once the suture is in place, adhesive tape is applied onto the skin to protect and adjust the skin edges or temporary nonabsorbable sutures can be applied on the skin in a running or interrupted manner.

In another embodiment of the invention, the sutures are inserted in an interrupted manner by inserting a surgical needle 10 with the attached gold suture 12 into the dermis 14 at one side 16 of the laceration, penetrating through the subcutaneous fat 18. The needle 10 is positioned vertically in the dermis 14 and inserted through the base 20 of the wound through part of the aponeurosis and then inserted through the subcutaneous fat 18 into the dermis 14 on the other side 24 of the laceration to form a loop under the skin and tightened by applying tension. A separate insertion is made approximately 3 to 5 mm from the previous loop and the intradermal suture loop technique is repeated. Once the sutures are in place, adhesive tape is applied onto the skin to protect and adjust the skin edges or temporary nonabsorbable sutures can be applied on the skin in a running or interrupted manner.

In another embodiment of the invention, the method may be used in hair transplant surgery. The suture is inserted into the dermis at one side of the wound, penetrating through the subcutaneous fat and the needle is positioned vertically between hair follicles 26. The same suture method describe in the foregoing is used.

By suturing the wound together under the surface of the skin, stitching through the skin is avoided and as a result the scarring is minimized. Additionally, the gold sutures are left in place permanently with little likelihood of infection or inflammation. The placement of the gold sutures also helps in the healing of the wound because the gold suture becomes covered with a thin connective tissue capsule to help hold the edges of the wound together.

Figure 3A:
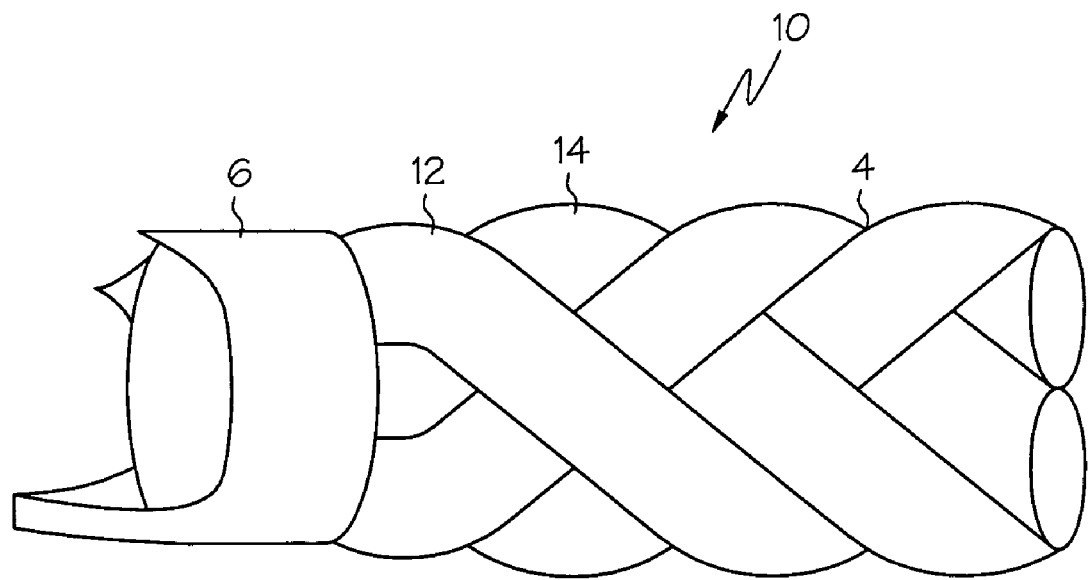
FIG. 3A is a view of the braided composite suture comprising a gold thread and a bioabsorbable attached to a needle.
Figure 3B:
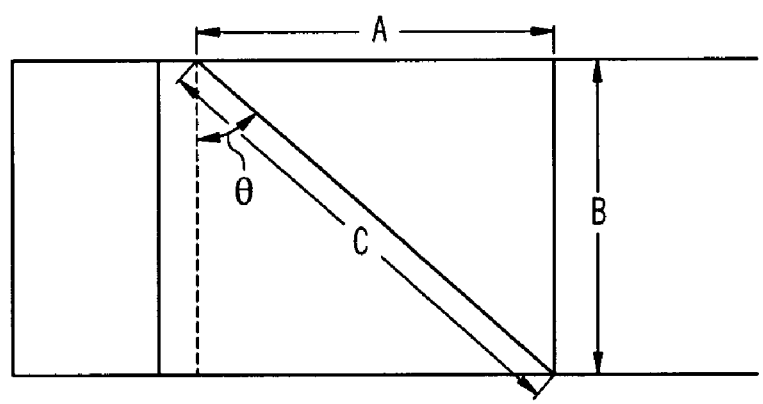
FIG. 3B is a graph showing the geometrical measurements of the braided suture.

The size and length of the suture will depend on the length of the wound, the width of tissue excised and the force of tension required. Thicker sutures may be used in wounds requiring higher tension. In the preferred embodiment of the invention, a braided suture comprising gold and bioabsorbable threads is used to perform the method of this invention. The suture may be braided very tightly or less tightly as desired; however, the suture is only required to be braided tight enough to maintain the braid. A tighter braid creates more zigzag pattern for the gold thread, once the bioabsorbable thread is absorbed, which then becomes covered with a thin connective tissue capsule to help hold the edges of the laceration together. FIG. 3A shows the braided composite suture 10 comprising a gold thread 12 and a bioabsorbable thread 14 attached to a needle 6. Additionally, grooves 4 are created by the braided structure of the suture 10. FIG. 3B shows the geometrical measurements of the suture. The pace of the braided structure is represented by A, the diameter of the suture is represented by B, the length of the thread in a pace A is represented by C and the braid angle is represented by $\theta$. Typically the suture is braided such that the braid angle $\theta$ is 45°. A more tightly braided suture will have a braid angle less than 45° while a looser braided suture will have a braid angle greater than 45°. Additionally, the tighter the braid of the suture, the less the length of the thread C in a pace A.

Because skin thickness and tissue tension will differ with each patient, the thickness of the suture will be used with respect to the thickness and tension of the patient's skin. In a manifestation of the preferred embodiment, the suture can range from 2 to 10 gauge in thickness. Generally, a suture with 10 gauge thickness would comprise about 3 threads, a suture between 4 to 6 gauge would comprise 5 to 6 threads and a suture between 2 to 4 gauge would comprise about 9 threads.

Braiding the bioabsorbable threads and the gold threads into a composite suture results in many advantages. After implanting the braided suture, the bioabsorbable thread becomes absorbed in the body, while the gold thread stays in place. The braided structure of the suture has several advantages over a regular suture in this procedure. The braided structure provides the suture with more flexibility to maneuver in surgical applications and furthermore, adds tensile strength to the suture which allows use in higher tension procedures. The braids also allows the sutures to be knotted and tied. Furthermore, the grooves from the braided configuration creates frictional communication as the suture is passed through the skin, providing adequate traction.

This method provides an efficient procedure for closing wounds, incisions and severed tissues such as tendons, joint capsules, aponeurosis and ligaments. Furthermore, the method may also be used to perform cosmetic surgeries such as hair restoration.

The invention claimed is:

1. A method of closing a skin laceration wherein the laceration extends through the dermis and the subcutaneous fat layer comprising:
   (a) providing a suture including at least one gold thread and at least one bioabsorbable thread braided together;
   (b) inserting the suture into the dermis and through the subcutaneous fat layer on one side of the laceration;
   (c) inserting the suture at the base of the laceration;
   (d) inserting the suture through the subcutaneous fat layer and into the dermis on the other side of the laceration to form a loop under the skin;
   (e) repeating the steps (b)–(d) in another insertion 3 to 5 mm from the loop to close the laceration; and (f) tightening the suture line by applying tension to the loops to bring one side of the laceration into contact with the other side of the laceration.

2. The method of claim 1 wherein step (e) of repeating the steps in another insertion 3 to 5 mm from the loop is performed in a continuous manner.

3. The method of claim 1 wherein step (e) of repeating the steps in another insertion 3 to 5 mm from the loop is performed in an interrupted manner and wherein step (f) of tightening the suture is performed following step (d).

4. The method of claim 1 wherein the base of the laceration is a part of the aponeurosis.

5. The method of claim 4 wherein the suture is tacked on the aponeurosis.

6. The method of claim 1 wherein knots are formed on both ends of the suture, leaving the entire suture under the skin.

7. The method of claim 1 wherein the suture is inserted between hair follicles in hair-bearing skin regions.

8. The method of claim 1 wherein the suture has a thickness in the range of 2 to 10 gauge.

9. The method of claim 8 wherein the suture is braided with 3 to 9 threads.

10. The method of claim 1 wherein the suture comprises 1 to 5 gold threads.

11. The method of claim 1 wherein the suture comprises 1 to 5 bioabsorbable threads.

12. The method of claim 1 wherein the suture comprises 50% gold threads and 50% bioabsorbable threads.

13. The method of claim 1 wherein the bioabsorbable threads can be selected from polymeric threads and non-polymeric threads.

14. The method of claim 1 wherein the gold threads are from different gold alloys.

15. The method of claim 1 wherein the suture is attached to different types of needles.

16. The method of claim 1 wherein the suture has a braid angle of 45 degrees.

17. A method for closing a laceration in a skin, wherein said laceration extends through a dermis and a subcutaneous fat layer, comprising:

(a) providing a suture, said suture including at least one gold thread and at least one bioabsorbable thread braided together;

(b) inserting said suture into said dermis and through said subcutaneous fat layer on a first side of said laceration;

(c) inserting said suture at a base of said laceration, wherein said base includes at least a portion of an aponeurosis;

(d) inserting said suture through said subcutaneous fat layer and into said dermis on a second side of said laceration;

(e) tightening said suture to bring said first side of said laceration generally into contact with said second side of said laceration, wherein said suture is positioned generally entirely below said skin; and (f) aligning said skin on said first side of said laceration with said skin on said second side of said laceration.

18. The method of claim 17 further comprising repeating steps (b)–(d) until said laceration is generally closed.

19. The method of claim 17 wherein said aligning step includes at least one of applying adhesive tape to said skin and applying temporary sutures to said skin.

* * * * *